(12) United States Patent
Saul

(10) Patent No.: US 9,057,724 B2
(45) Date of Patent: Jun. 16, 2015

(54) DETECTING A HIGH MOLECULAR WEIGHT SUBSTANCE

(75) Inventor: Steven J. Saul, Arlington, MA (US)

(73) Assignee: Charm Sciences, Inc., Lawrence, MA (US)

( * ) Notice: Subject to any disclaimer, the term of this patent is extended or adjusted under 35 U.S.C. 154(b) by 46 days.

(21) Appl. No.: 14/118,333

(22) PCT Filed: May 23, 2012

(86) PCT No.: PCT/US2012/039059
§ 371 (c)(1),
(2), (4) Date: Feb. 24, 2014

(87) PCT Pub. No.: WO2012/162346
PCT Pub. Date: Nov. 27, 2012

(65) Prior Publication Data
US 2014/0206100 A1    Jul. 24, 2014

Related U.S. Application Data

(60) Provisional application No. 61/489,196, filed on May 23, 2011, provisional application No. 61/489,617, filed on May 24, 2011, provisional application No. 61/495,131, filed on Jun. 9, 2011.

(51) Int. Cl.
*G01N 33/558* (2006.01)
*G01N 33/543* (2006.01)
*G01N 33/58* (2006.01)

(52) U.S. Cl.
CPC .... *G01N 33/54393* (2013.01); *G01N 33/54366* (2013.01); *G01N 33/54346* (2013.01); *G01N 33/585* (2013.01); *G01N 33/543* (2013.01); *G01N 33/558* (2013.01); *G01N 2333/4713* (2013.01); *G01N 2333/4731* (2013.01)

(58) Field of Classification Search
CPC .......... G01N 33/558; G01N 33/54366; G01N 33/585; G01N 33/543; G01N 33/54346
USPC ................. 436/514, 518, 501, 533, 534, 432; 435/7.1, 7.92, 287.1, 7.94, 970, 287.2, 435/287.7, 287.8, 287.9, 973; 422/412, 422/423, 424, 68.1
See application file for complete search history.

(56) References Cited

U.S. PATENT DOCUMENTS

| | | | |
|---|---|---|---|
| 5,965,453 A | 10/1999 | Skiffington et al. | 436/165 |
| 5,985,675 A | 11/1999 | Charm et al. | 436/514 |
| 6,319,466 B1 | 11/2001 | Markovsky et al. | 422/56 |
| 7,410,808 B1 | 8/2008 | Saul et al. | 436/514 |
| 7,749,776 B2 * | 7/2010 | Lamotte | 436/532 |
| 7,785,899 B2 | 8/2010 | Saul et al. | 436/518 |
| 7,863,057 B2 | 1/2011 | Saul et al. | 436/518 |
| 2008/0274566 A1 * | 11/2008 | Saul et al. | 436/518 |
| 2010/0279310 A1 * | 11/2010 | Sia et al. | 435/7.1 |
| 2011/0070127 A1 * | 3/2011 | Saul et al. | 422/69 |

* cited by examiner

*Primary Examiner* — Melanie Y Brown
*Assistant Examiner* — Erik B Crawford
(74) *Attorney, Agent, or Firm* — MacCord Mason PLLC; Richard J. Long

(57) ABSTRACT

Label complexes, lateral flow apparatus and methods of detecting a high molecular weight substance are shown and described. In one embodiment, the label complex includes an antispecies antibody and another antibody having sensitivity to both the antispecies antibody and to a control line capture agent, an antibody binding protein and a detectable component. Typically, the antibody binding protein may bind to a receptor for the analyte or to the anti-species antibody. In yet other embodiments, a lateral flow test strip includes the label complex and a solid support that traverses lateral flow of a liquid sample and provides a detectable signal.

11 Claims, 8 Drawing Sheets

DETECTING A HIGH MOLECULAR WEIGHT SUBSTANCE

RELATED APPLICATIONS

This application claims priority to PCT application to PCT/US2012/39059, filed May 23, 2012; U.S. provisional application 61/489,196, filed May 23, 2011; U.S. provisional application 61/489,617 filed May 24, 2011; and U.S. provisional application 61/495,131, filed Jun. 9, 2011, all of which are incorporated herein by reference in their entireties.

FIELD OF THE TECHNOLOGY

The present disclosure relates generally to detecting high-molecular weight substance, and more particularly, to improved label complexes, lateral flow apparatuses and methods for detecting the presence of one or more high molecular weight analytes.

BACKGROUND

Several tests to detect analytes in samples are known in the art. Some examples are described in U.S. Pat. No. 5,985,675, issued Nov. 16, 1999; U.S. Pat. No. 6,319,466, issued Nov. 20, 2001; U.S. patent application Ser. No. 10/289,089, filed Nov. 6, 2002 (based on U.S. Provisional Application 60/332,877, filed Nov. 6, 2001); U.S. patent application Ser. No. 09/961,998, filed Sep. 24, 2001; U.S. Pat. No. 7,410,808, issued Aug. 12, 2008; U.S. Pat. No. 7,785,899, issued Aug. 31, 2010; and U.S. Pat. No. 7,863,057, issued Jan. 4, 2011, all of which are incorporated herein by reference in their entireties and elements of which may be useful in embodiments described herein. Sample and testing devices and methods are also known in the art including those described in U.S. Pat. No. 5,965,453, issued Oct. 12, 1999, incorporated herein by this reference in its entirety and elements of which may be useful in embodiments described herein.

Tests to detect one or more analytes in a sample using receptors, such as antibodies, that include detectable components can be designed in variety of formats. One such format is known as a sandwich assay. In a typical sandwich assay format the analyte to be detected becomes bound by two receptors, one of which carries a detectable component—the label receptor—and the other of which captures the analyte to allow detection. Sandwich assays, however, are known to exhibit what is known in the art as a hook effect. The hook effect is a characteristic of a sandwich assay which is observed at higher concentrations of an analyte that is being detected. The hook effect can be caused by an overwhelming of a capture agent by unlabeled analyte thereby blocking detection of labeled analyte. The hook effect can, therefore, lead to a false negative result. Applicant has discovered that it is advantageous to provide a test that does not suffer from the hook effect and that can detect large molecules, such as proteins, including allergenic proteins, in a sample, such as a food sample.

Separate from the hook effect, is the problem of steric hindrance which is sometimes observed in lateral flow tests, and other tests detecting high molecular weight molecules, such as molecules of molecular weight greater than about 5,000, such as proteins, for example casein and beta-lactoglobulin. In particular, effective functioning of the test can be impaired by the interference of the large molecule with binding sites when protein binding is being detected, or when a large molecule is involved in a test in general. Applicant has discovered that it is advantageous to provide a test that can detect large molecules, such as allergenic proteins, in a sample, such as a food sample, that does not suffer from such steric hindrance or, at least, reduces the influence of steric hindrance.

Therefore, Applicants desire systems and methods for detecting high-molecular weight substance without the drawbacks presented by the traditional systems and methods.

SUMMARY

In accordance with the present disclosure, a label complex and lateral flow apparatus is provided for detecting at least one high-molecular weight substance. This disclosure provides an improved lateral flow device that is convenient, efficient, and safe for the user without the drawbacks of the hook effect and steric hindrance, particularly when used to detect allergenic proteins. This disclosure may allow for a method of detecting high-molecular weight substance with the label complex and lateral flow apparatus described herein.

In one embodiment, in a lateral flow test apparatus having at least one test area and at least one control area including a control area capture agent for the detection of at least one analyte in a sample, a label complex includes at least two antibodies, an antibody binding protein and a detectable component. One of the at least two antibodies may include an antispecies antibody, while the other of the at least two antibodies includes an antibody having a sensitivity to the control area capture agent. Typically, the capture agent is bound to the at least one control area. Further, the antibody binding protein may be adapted to bind to a receptor for the analyte and to the anti-species antibody. The detectable component may be bound to the antibody binding protein.

In some examples, the control area capture agent may be characterized by an affinity to the label complex that is independent of the label complex being bound by the analyte. The antibody binding protein may be protein A. The receptor for the analyte may be an antibody. The detectable component may be a gold particle. The receptor for the analyte may be an antibody that is linked to the detectable component, such as through an antibody binding protein.

In another embodiment, a lateral flow test strip for the analysis of an analyte in a liquid sample includes a label complex and a solid support. The label complex may include at least two antibodies, an antibody binding protein and a detectable component. One of the at least two antibodies may include an antispecies antibody, while the other of the at least two antibodies includes an antibody having a sensitivity to the control area capture agent. Typically, the capture agent is bound to the at least one control area.

Further, the antibody binding protein may be adapted to bind to a receptor for the analyte and to the anti-species antibody. The detectable component may be bound to the antibody binding protein. The solid support may support the label complex, the control line and at least one test line. Further, the solid support may include a body that is adapted to traverse lateral flow of the liquid sample and provide a detectable signal. Typically, the detectable signal has an intensity provided when an analyte receptor is captured by either the control line capture agent or a test line capture agent.

In some examples, a greater intensity of the detectable signal in the test line, as compared to the control line, indicates a negative result. Similarly, a greater intensity of the detectable signal in the control lines compared to the test line indicates a positive result. The test line capture agent may be immobilized on the solid support in a test line. The test line capture agent may be characterized in that the capture agent has greater binding affinity to the label complex when the label complex is unbound by an analyte. The analyte receptor may include an antibody with sensitivity to the analyte. The test line capture agent may include a representative analyte, or analog thereof. The analyte may be casein, and the analyte receptor may be an antibody to casein. The analyte may be beta-lactoglobulin and the analyte receptor may be an antibody to beta-lactoglobulin.

In other examples, the test strip is adapted to detect casein and beta-lactoglobulin and comprises two analyte receptors and two test lines. At least one of the analyte receptors may comprise antibody to casein, while at least one of the other analyte receptors may comprise antibody to beta-lactoglobulin. In yet a further example, the test strip may be adapted to detect casein and beta-lactoglobulin and comprises two analyte receptors and two test lines. The at least one of the analyte receptors comprises antibody to casein, while the other analyte receptor comprises antibody to beta-lactoglobulin. Further, the device may include at least two test lines, wherein one test line comprises a capture agent with sensitivity to the antibody to casein, and the other test line comprises capture agent with sensitivity to the antibody for beta-lactoglobulin.

In one particular method embodiment, detecting of at least one analyte in a sample on an apparatus having at least one test area and at least one control area on a solid support and a label complex includes applying an admixture of a receptor for the at least one analyte and the sample to the solid support to create a mobile phase, generating a detectable signal at the at least one test area, generating a detectable signal at the at least one control area and comparing the intensity of the detectable signal at the at least one test area and the control area.

In some examples, the mobile phase may comprise the admixture and the label complex. The receptor binding to the analyte may form an analyte-receptor complex. The label complex may include at least two antibodies. In particular examples, the label complex is characterized by an ability for binding to the receptor to provide, in the mobile phase, a receptor-label complex. Further, the label complex is characterized by ability for binding to the receptor-analyte complex for providing, in the mobile phase, an analyte-receptor-label complex. The label complex may also be characterized by the ability to generate a detectable signal.

In yet other examples, the at least one test area comprises a test area capture agent that is generally immobilized on the solid support. The test area capture agent may have a greater binding affinity to the receptor-label complex than to the analyte-receptor-label complex. Further, the control area may comprise a control area capture agent. Typically, the control area capture has an affinity to the receptor-label complex that is independent of the receptor-label complex being bound by analyte.

In yet another embodiment, a method for the analysis of one or more analytes in a liquid sample includes applying an admixture, allowing the mobile phase to flow to at least one test line, allowing the mobile phase to flow to a control line and then measuring the intensity of the detectable signal at each of the at least one test line and the control line. Typically, the admixture comprises a receptor for an analyte and a sample to a solid support to create a mobile phase. The receptor may be characterized by an ability to bind to the analyte to form an analyte-receptor complex. The solid support may be configured for lateral flowing of the mobile phase on the solid support. The mobile phase may include both the admixture and a label complex.

In some examples, the label complex is characterized by: an ability to bind to the receptor to provide, in the mobile phase, a receptor-label complex; the presence of more than one antibody; an ability to provide a detectable signal on the test strip; and/or an ability to bind to the receptor-analyte complex to provide, in the mobile phase, an analyte-receptor-label complex.

The at least one test line may comprise a test line capture agent immobilized on the solid support. The test line capture agent may be characterized in that the capture agent has greater binding affinity to the receptor-label complex than to the analyte-receptor-label complex. A control line capture agent characterized in that it has affinity to the receptor-label complex whether or not the receptor-label complex is bound by analyte from the sample. Typically, a greater intensity of the detectable signal in any one test lines, as compared to the control line, indicates a negative result for a particular analyte. Conversely, a greater intensity of the detectable signal in the control line, as compared to any one test line, indicates a positive result for a particular analyte.

In particular examples, the method includes combining the receptor for an analyte with the sample to create the admixture. The receptor may comprise an antibody with sensitivity to the analyte. The label complex may comprise an antibody binding protein. Typically, the label complex comprises two antibodies, one of the two antibodies is capable of binding at the control line, while the other of the two antibodies is capable of binding to the labeled antibody binding protein. Further, the test line capture agent may comprise a representative analyte or analog thereof. The admixture may be incubated prior to applying to the solid support. Additionally, the at least one test line may comprise at least two test lines, wherein one of the two test lines measures casein and the other measures beta-lactoglobulin.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
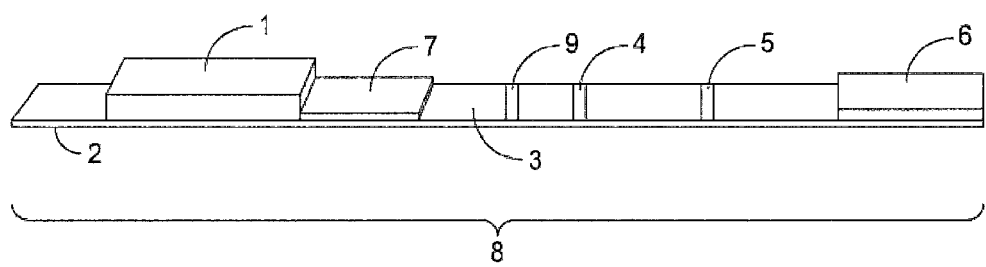
FIG. 1 is a side perspective view of a test strip according to an embodiment of the disclosure having two test areas and a control area.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 2:
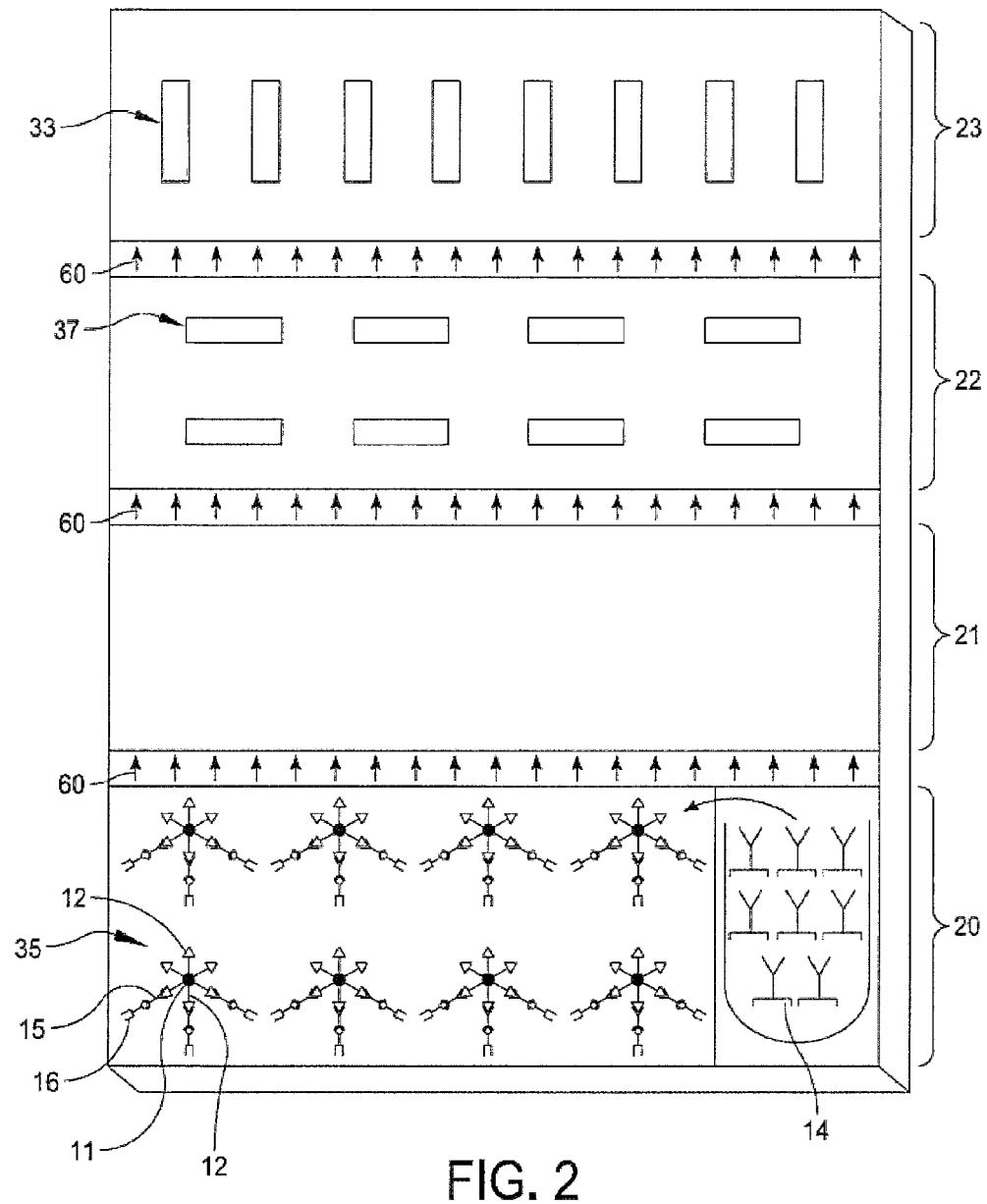
FIG. 2 is an isolated schematic view of test strip components and a label complex of the embodiment of FIG. 1 prior to application of sample solution.

Referring now to the drawings in general and FIGS. 1 and 2 in particular, it will be understood that the illustrations are for the purpose of describing embodiments of the disclosure and are not intended to limit the disclosure or any invention thereto. As best seen in FIGS. 1 and 2, a test strip lateral flow apparatus 8 with label complex 35 is shown embodied according to the present disclosure. As illustrated herein, embodiments of the lateral flow test apparatus typically include a testing area, a control area and a label complex, for instance in an application area, whereby flow across the apparatus to the testing and control areas provides an arrangement capable of generating a detectable signal. FIG. 1 shows one embodiment of a test strip apparatus 8, comprised of a membrane, for instance a nitrocellulose membrane 3, POREX 7, a sample application pad 1, and a disposal pad 6 attached to a solid support 2. Generally, the test strip apparatus 8 includes a testing area, for instance test line 4, and a control area, for instance control line 5. The label complexes, lateral flow apparatus and methods described herein have been found unexpectedly useful to detect one or more substances (i.e. analytes), and in particular proteins, such as allergenic proteins.

Typically, sample is contacted to an application area, for instance at sample application pad 1 at one distal end of the test strip 8, as illustrated in FIG. 1. However, other embodiments include contacting sample to one or more application areas at a variety of locations on the apparatus, so that flow will generally follow the downstream (downstream refers to the general sequential flow path described herein, and is not to be construed by any elevational drop unless specified) flow across the various components discussed herein. As shown, sample flows from sample application pad 1 to POREX 7 containing mobile phase receptor. A portion of receptor will bind analyte from the sample and flow along the nitrocellulose membrane 3 to at least one test line 4. A portion of receptor unbound by sample analyte will bind to at least one of the test lines 4. The remaining unbound receptor and analyte-receptor complex will then flow downstream to at least one control line 5. A portion of the unbound receptor and a portion of analyte-receptor complex may then bind at the at least one control line 5. The remaining unbound receptor, or analyte-receptor complex, will flow downstream to the absorbent pad 6. Generally, to determine a result, a detectable signal at the control area, for instance at a control line 5, is compared to a detectable signal at the test area, for instance at the test line 4.

The lateral flow apparatuses described herein generally have sufficient inherent strength to support the various components described herein. Yet in particular examples, the lateral flow apparatus includes a supplemental support, such as a plastic backing upon which porous or bibulous strip components are attached or the like, for additional support strength. As shown in FIG. 1, the lateral flow test strip 8 upon which the various reagents and/or sample described herein are applied can be wholly, or partially, porous or bibulous so that the mobile phase can flow on the lateral flow apparatus, through the apparatus or otherwise transverse the apparatus. In one example, the lateral flow strip 8 is constructed wholly, or partially, of a material that can bind proteins, such as carrier proteins, including bovine serum albumin (BSA) and ovalbumin (OVA). For instance, the lateral flow strip 8 may be constructed of a nitrocellulose material or the like. However, other examples of the lateral flow apparatus include a variety of materials in various portions of the apparatus, including natural or synthetic materials.

In some examples, the lateral flow apparatus, including test strip 8, includes cellulosic materials such as paper, cellulose and cellulose derivatives such as cellulose acetate and nitrocellulose; fiberglass; glass fiber filter, for example WHATMAN Fusion 5 membrane (Whatman is a registered trademark of Whatman paper Limited, Kent, England); cloth, both naturally occurring and synthetic; porous gels such as silica gel, agarose, dextran and gelatin; porous fibrous matrices; starch based materials, such as cross-linked dextran chains; ceramic materials; films of polyvinyl chloride and combinations of polyvinyl chloride-silica; POREX (Porex is a registered trademark of Porex Technologies Corp., Fairburn, Ga.), mixtures thereof and the like. Regardless of the material selected, the lateral flow apparatus material generally provides the downstream flow described herein, so that the flow stream allows liquid to flow on or through the lateral flow apparatus. If a variety of materials are used, the variety of materials are generally in fluid flow communication/contact with one another, or otherwise capable of being brought into fluid flow communication/contact as discussed herein.

The lateral flow apparatus may include a predefined application area. As shown in FIG. 1, the test strip 8 includes an application pad 1 that is in fluid flow communication/contact with a first end of the test strip 8, for instance at the distal end of the strip. In particular examples, contact, i.e. application of the sample to the application pad, can be through direct contact to the sample application pad 1. In yet other examples, contact may be made through an intermediate material allowing flow between the application pad 1 and other portions of the lateral flow apparatus, as described hereinafter. Typically, the fluid flow communication/contact is such that the test sample migrates from the application pad 1 to the other portions downstream of the application pad 1. In yet other examples, in addition to receiving the sample, the application pad 1 also drives fluid flow along the strip 8. For instance, particles that are above a certain size, as recognized by those skilled in the art, may clog the strip pores and/or may interfere with flow due to affinity to strip components, thereby invalidating test results or otherwise reducing test function. Therefore, the application pad 1, and other strip components described hereinafter, may also filter and remove unwanted elements from the sample, such as unwanted particles.

FIG. 1 shows the membrane 3 on the lateral flow test apparatus. In particular examples, the membrane 3 includes beads, and the membrane 3 containing the beads may be pretreated with a blocking solution. The blocking solution may dissolve when the diluted sample is added to the apparatus. Similarly, the nitrocellulose membrane can also be pretreated and/or blocked.

FIG. 1 also illustrates one embodiment of the test strip 8, wherein at least one test line 4 and at least one control line 5 are positioned downstream of the application area, and of one another. Although not clear from FIG. 1, the two test lines and the one control line may be evenly spaced from one another, however other examples include the test lines and control lines being spaced in other variations. Therefore, embodiments include a variety of test area and control area orientations along the strip 8. In that respect, the spacing distance between the lines, or test and control areas, for instance the spacing may be varied to adjust assay time, i.e. larger distances to increase assay time as the flow traverses downstream and the like. The sensitivity of the assay may also change depending on line positioning and, therefore, reagent titration can be adjusted to accommodate these differences or assay requirements.

Embodiments of the lateral flow test apparatus include multiple test lines within a test area, each test line being capable of capturing the analyte-receptor discussed below. As shown in FIG. 2, the multiple test lines may each contain the same, or substantially similar, concentration of capture agent 37. However, in other examples, the test lines may contain different concentrations of capture agent 37. For example, the first test line may have a lower concentration of capture agent as compared to the second test line. Such a configuration will accommodate the fact that analyte-receptor arrives at the first test line earlier and, therefore, everything else being equal, more binding will tend to occur in the first test line as compared to the second test line. That is, with an equal amount of capture agent 37 at each line, there would be more receptor available for binding to the first test line which would result in more binding to the first test line, as compared to the second test line. Yet in other examples, capture agent 37 may be titrated accordingly. In additional examples with multiple test lines to capture multiple receptors, and, thereby, detecting multiple analytes, each test line can have a different capture agent, including any of the capture agent examples described herein.

As shown in FIG. 1, the lateral flow apparatus includes a control area, for instance a control line 5 that is positioned downstream of the application area and from the test areas. Typically, the control line 5 is used for comparison to at least one, or more, test lines. Further, the control line 5 may signal that the test functioned properly and/or is complete. In particular embodiments, the control line 5 includes a substance, such as a control line capture agent 33 introduced in FIG. 2, that has affinity to both the label complex unbound by analyte from the sample and the label complex bound by analyte from the sample.

In some embodiments, the control line capture agent 33 includes a capture agent with affinity to the antibody attached to an antispecies antibody on the protein A. In particular examples, the control line capture agent is cloxacillin that is bound to the test strip 8 using BSA, and the antibody attached to the anti-species antibody is an antibody to cloxacillin. Some useful antibody binding proteins include protein A, protein G or protein AG and recombinant forms of the same. Further, when analyte receptor, discussed hereinafter, is an antibody, or fragments thereof, the capture agents can include antigens with an affinity to the antibody. For instance, antigens include analogues thereof, or any substance exhibiting affinity to the receptor that is similar to that of the analyte.

One embodiment for the detection of multiple analytes is shown in FIGS. 1 and 2. Here, the lateral flow apparatus includes two analyte-receptors 14 and two test lines 4 and 9 being employed to capture the label complex 35 in the separate lines within the test area. In an example in which casein and beta-lactoglobulin are detected, antibody to casein, and antibody to beta-lactoglobulin are the analyte receptors.

In one example, antibody to casein, and antibody to beta-lactoglobulin may be mixed with the sample and incubated prior to application to the test strip 8. In this particular example, the first test line capture agent 37 includes the immobilized casein and the second test line capture agent 37 includes an immobilized beta-lactoglobulin, or vice versa. Such positioning, including attachment, at the test line 22 generates a visible signal when a detectable component, such as gold, is captured. In other embodiments, a single control line 23 is employed for comparison. In yet additional embodiments, multiple control lines 23 may be positioned on the test apparatus.

Unexpectedly, it has been uncovered that even if antibody for the control line capture agent can be bound directly to antibody binding protein, it may remain desirable to use an intermediate anti-species antibody 15. For example, the size of the analyte, such as casein, beta-lactoglobulin, and/or other proteins and other analytes of interest, may cause interference with binding. For instance, there may be interference in control line binding due to steric hindrance of a binding site by the large molecule. Adding anti-species antibody 15 may create a spacer arm to provide additional space between the control line binding site on the antibody to the control line capture agent 33 and the analyte that might be attached to the analyte receptor 14 on the label complex 35. The antibody to the control line capture agent 33 may therefore function as a spacer arm in that it can stick out further from the gold label than the antibody for the analyte, even when the antibody for the analyte is bound by analyte.

In embodiments having the competitive-type assay described herein, along with the label complex that includes the optional spacer arm (in embodiments described herein the spacer arm is described as an anti-species antibody 15, however, other possible spacer arms are useful if they accomplish the same goal), steric hindrance by the large molecular weight analyte can be lessened, or even prevented. Further, in these embodiments, hook effect at high concentrations of analyte is also reduced, if not avoided.

As introduced above, the lateral flow apparatuses, including the test strip 8 shown in FIG. 1, include a stationary phase and a mobile phase. For instance, the POREX 7 may contain a mobile phase receptor (as later shown in FIG. 2). The stationary phase can include various reagents immobilized on the test strip 8. Stationary phase reagents, sometimes referred to as a capture agent (as later illustrated as test line capture agent 37 and control line capture agent 33) can be immobilized on the test strip 8 so that they capture substances from the mobile phase. As a result, signal is generated by a reagent from the mobile phase, alone or by a reaction with other reagents. The reagent providing the signal is often referred to herein as the detectable component. The detectable component can be configured to provide a signal simply by being captured on the test strip 8, for example gold sol particles. The detectable component can also include reagents that require a binding reaction, such as an enzyme-substrate reaction, to provide the detectable signal. Various suitable detectable components include chromogens, catalysts, fluorescent compounds, chemiluminescent compounds, radioactive compounds, magnetic beads or magnetic particles, enzymes or substrates, vesicles containing signal producing substances, colorimetric compounds, direct visual detectable components including colloidal metallic and metallic and non-metallic colored particles, dye particles, or organic polymer latex colored particles.

FIG. 2 shows one embodiment of a label complex 35 on a lateral flow test apparatus, for instance test strip 8, in area 20 and a plurality of analyte receptors 14. The label complex 35 and analyte receptor 14 may be mixed in a variety of configurations. For instance, in some examples, the analyte receptor 14 may be mixed with the label complex either before addition of label complex 35 and analyte receptor 14 to a test strip, yet in other examples the mixing may occur during addition to a test strip, yet in additional embodiments, the mixing occurs after addition to a test strip 8. For example, label complex 35 can be provided on a test strip 8 to be resolubilized by a sample/analyte receptor 14 mixture to form a mobile phase.

FIG. 2 illustrates that test line 22 includes at least one test line capture agent 37, and control line 23 includes at least one control line capture agent 33. As shown in FIG. 2 and later enlarged in FIG. 6, the label complex 35 in area 20 typically includes an antibody binding protein 12 that is both free and bound by anti-species antibody 15, antibody to control line capture agent 16 that is bound to anti-species antibody 15 and label 11. Analyte receptor 14 and label complex 35 combine with sample to form a mobile phase that includes label complex 35 bound to analyte receptor 14 through the interaction with antibody binding protein 12. The mobile phase typically flows in the downstream direction of the arrows 60.

Generally, as shown throughout the various FIGS. 2-9, embodiments of the label complex 35 include multiple binding sites for a variety of reagents and binding components. For example, a gold sol particle can be the detectable component that is linked to antibody binding protein, such as protein A, to form a labeled-protein A. Linking antibody binding protein 12 to gold, or similar labels, provides a bridge to link additional antibody. In an exemplary embodiment, an anti-species antibody 15, such as a rabbit anti-mouse antibody, is linked to the labeled-protein A. Such labeled protein A can be configured to allow not only the anti-species antibody 15 to bind to it, but also the analyte receptor 14, for example an analyte antibody previously mixed and incubated with the sample. Further, additional antibody, such as antibody from a species to which the anti-species antibody has affinity, can be linked to the antispecies antibody. The result can be a label complex that includes both analyte receptor, in this case antibody to the analyte to be detected, and an additional antibody. In one example, the additional antibody is selected and configured to have affinity to a control line capture agent 33.

The mobile phase can include the fluid sample that flows on and/or through the test strip 8. In some examples, the mobile phase can also include solutions, such as dilution buffer and/or extraction buffer. Buffers, such as extraction buffer, can be useful in a variety of cases, including when the sample is not initially in liquid form, or not completely in liquid form.

Mobile phase reagents include at least one or multiple analyte receptors 14. For instance, when multiple receptors are used, multiple analytes may be detected. Receptors 14 may be selected for their affinity to a target analyte, for example antibody to the analyte to be detected. As discussed hereinafter, pre-incubation of the sample may assist binding of the large analyte, such as a protein, with its related antibody.

Analyte receptor may be arranged to flow in the mobile phase and be captured by a stationary phase reagent. Typically, the receptors are captured at test and control areas, including at least one test line and at least one control line. As introduced above, either the test line or control line may include one or multiple capture agents. Again, the figures herein refer to test lines and control lines, but other embodiments include a variety of configurations, such as dots, lines areas, zones, all of which may be interchangeably employed. For example, a test area, or zone, can include multiple test lines or combinations of dots and lines. When multiple analytes are detected multiple test lines and/or multiple control lines can be used. Alternatively, a single control line can be used with multiple test lines or a single test line with multiple control lines.

Stationary phase capture agents may be previously immobilized onto the test strip 8 in either, or both, the test lines and control line. Capture agent immobilization to the test strip can be through protein interaction with the solid support 2, while other examples include various other immobilization techniques recognized in the art. For example, nitrocellulose can be employed for its protein binding capacity. Capture agent immobilization can also be through size limitation immobilization. The label complex can be detected when captured by the immobilized capture agent in the test line or control line.

In some examples, a portion of receptor will bind analyte from the sample and flow along the nitrocellulose membrane 3 to test line 4. A portion of receptor unbound by sample analyte will bind to the test lines. Remaining unbound receptor and analyte-receptor complex will flow to control line 5. A portion of said unbound receptor and a portion of analyte-receptor complex, will bind at the control line 5. Remaining unbound receptor or analyte-receptor complex will flow to the absorbent pad 6. In particular examples, the control line is compared to the test lines to determine a result.

The mobile phase can also include one or a variety of reagents (reagents are sometimes herein referred to in the singular, plural or as reagent(s). No difference is meant to be implied by the usage of singular, plural or both. In every case, the meaning can be any of those possibilities. The mobile phase may be produced from the addition of the sample to the test strip 8, whereby the liquid sample reconstitutes reagents previously placed, or otherwise secured, on the test strip 8. The mobile phase can also be produced from the addition of reagent, in liquid form, to the test strip 8. Such reagent can be combined with the sample prior to addition to the test strip 8.

Figure 3:
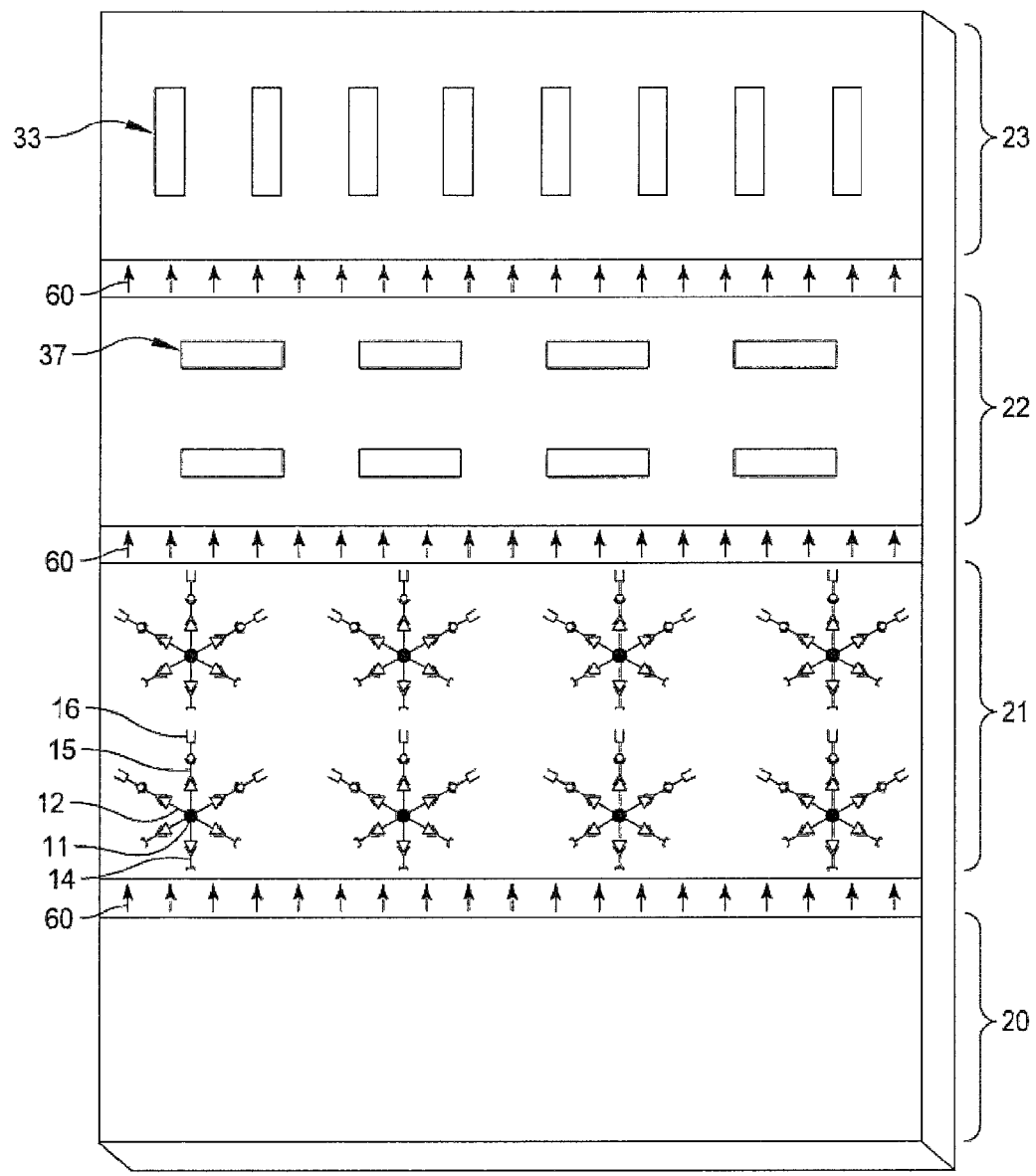
FIG. 3 is another isolated schematic view of test strip components of the embodiment of FIG. 1 after the addition of sample and analyte receptor.

FIG. 3 is a test strip schematic showing one embodiment of the label complex after binding to analyte receptor 14, for instance as later enlarged in FIG. 7. Analyte receptor 14 has affinity to both the analyte and test line capture agent 37. Such an affinity to both the analyte and to the test line capture agent 37 allows for competition in the sense that if the analyte from a sample does not bind to the analyte receptor 14, the analyte receptor 14 will be available to bind to the capture agent 37 on test area 22. Test area 22 includes test line capture agent 37, while downstream the control area 23 includes control line capture agent 33.

Figure 4:
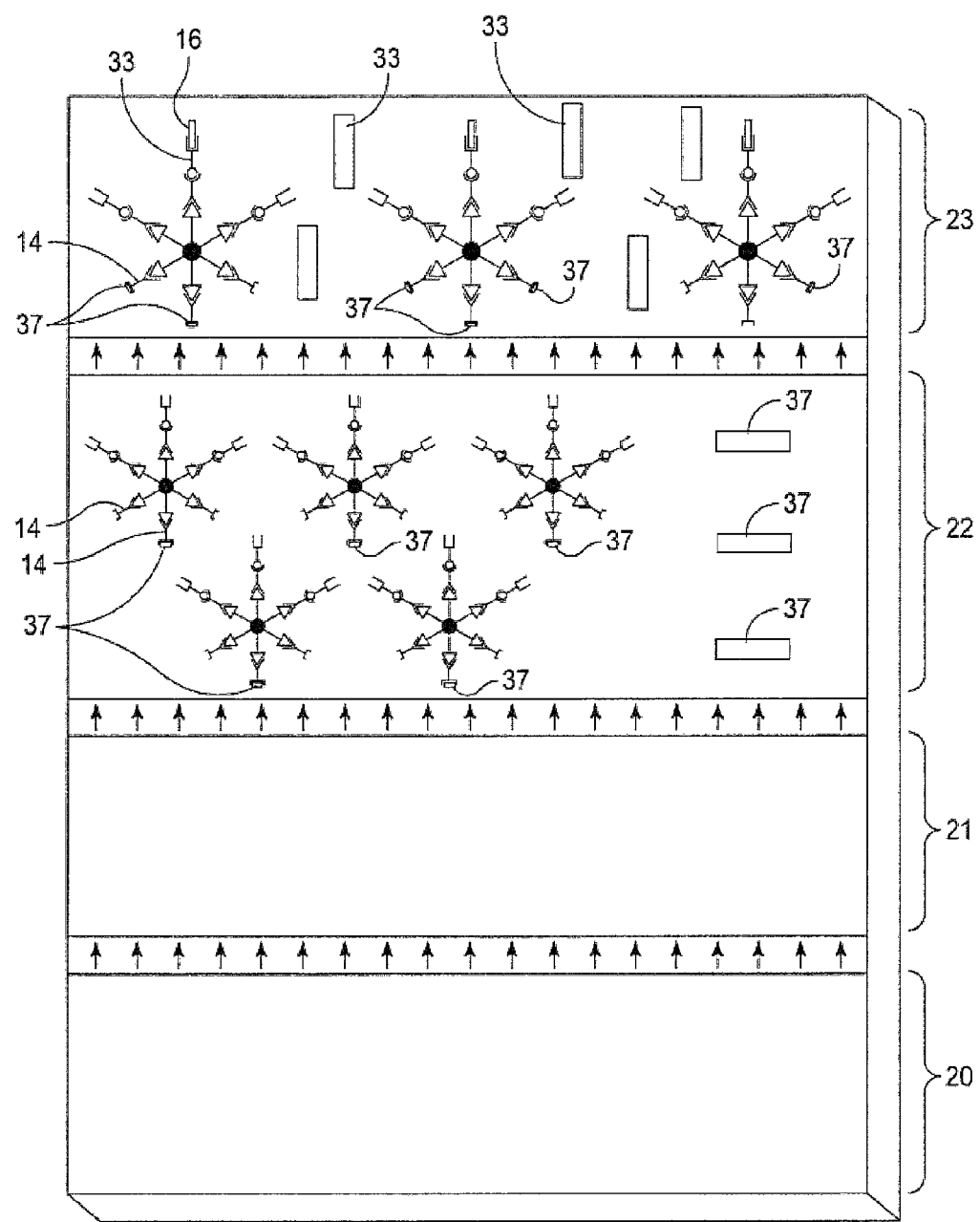
FIG. 4 is another isolated schematic view of test strip components, showing a test that is negative for analyte.

FIG. 4 is one test example representative of a negative result. As shown, the label complex is bound to analyte receptor 14 and having flowed to test area 22. Generally, because the analyte 37 is substantially bound to receptor 14, less binding is available at test area 22 as compared to being bound at control area 23. In this respect, the analyte from the sample "competes" with test line capture agent 37. If the analyte from the sample has bound sites on the analyte receptor 14, analyte receptor 14, and, therefore, label complex 35 bound thereby, will be unavailable or, if not all sites are bound, have reduced availability to bind to test line capture agent 37. Typically, both the analyte and the test line capture agent have a similar binding affinity to the analyte receptor, and are therefore similarly labeled 37 in particular examples and illustrations herein. Generally, FIG. 4 shows more binding of the label complex at the test area 22 as compared to control area 23 indicating a negative result.

Figure 5:
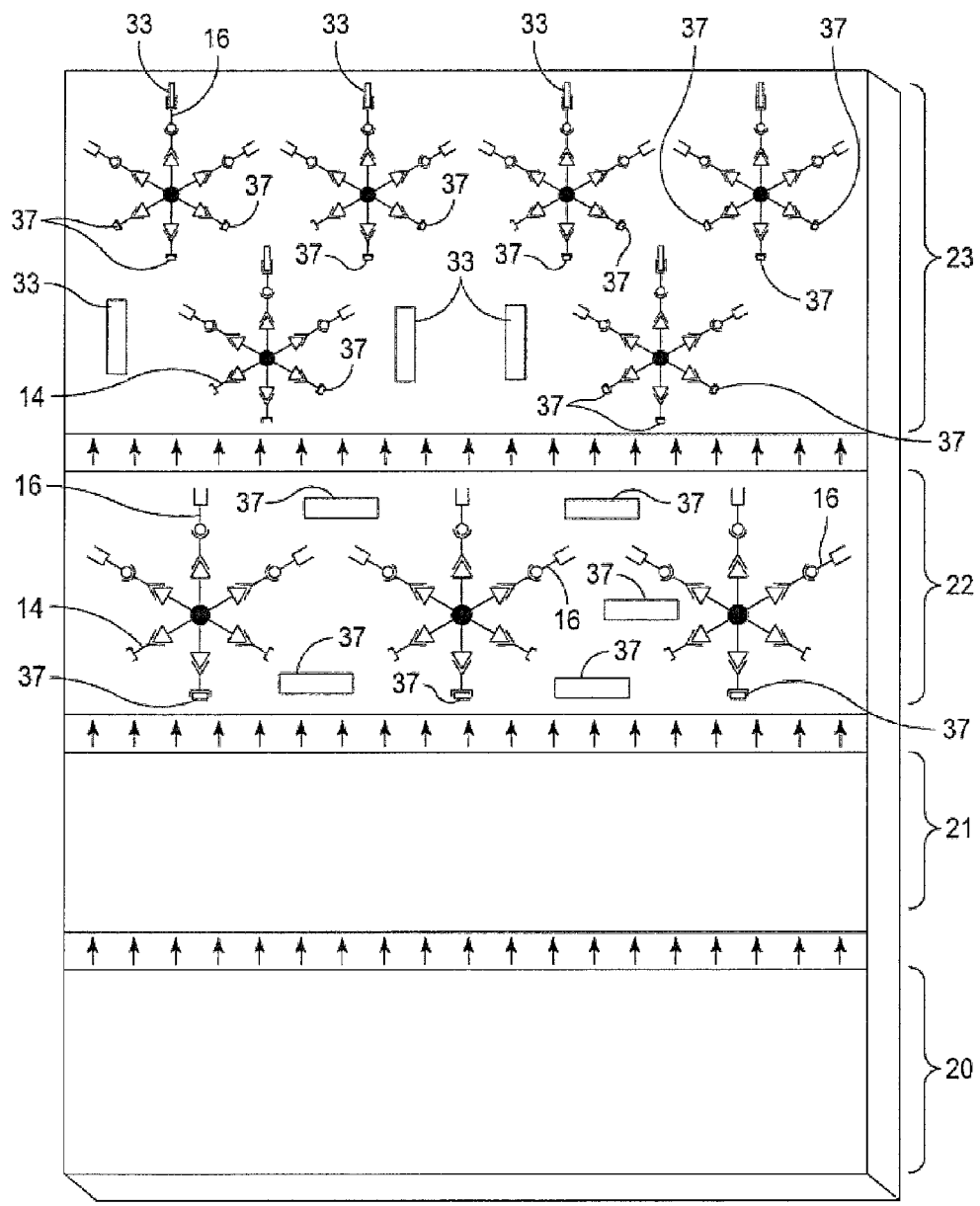
FIG. 5 is yet another isolated schematic view of test strip components, showing a test that is positive for analyte.

FIG. 5 is one test example representative of a positive result. FIG. 5 shows more binding of label complex 35 at control area 23 as compared to test area 22, indicating a positive result. As discussed above and illustrated in FIG. 5, analyte 37 bound to analyte receptor 14 through competitive inhibition causes label complex 35 to not be captured at test area 22, and to instead flow to control area 23 for binding. As a result, this detectable signal indicates a positive result.

Figure 6:
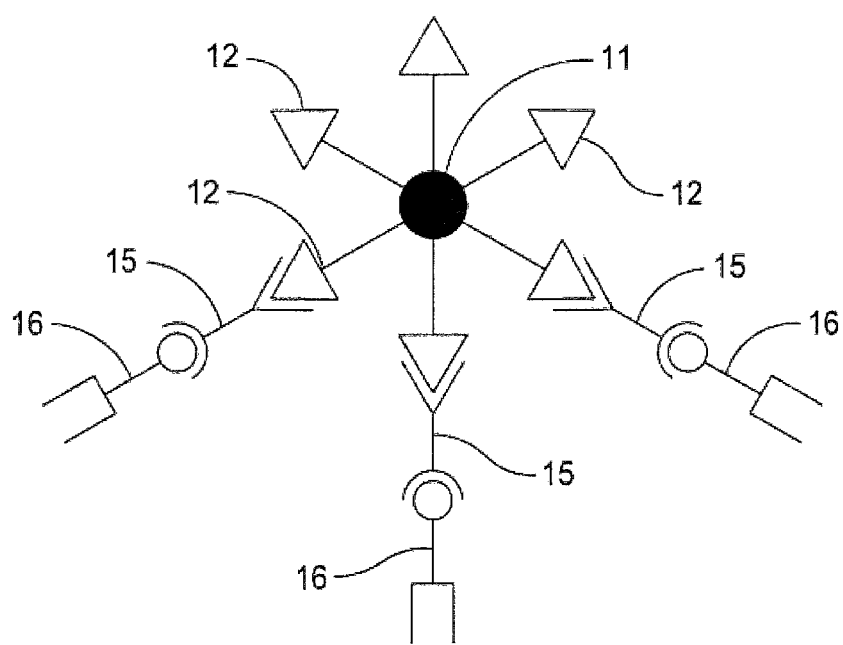
FIG. 6 is an isolated schematic view of a label complex embodiment.

FIG. 6 shows one embodiment of an analyte receptor label complex with label 11 and antibody binding protein 12. Label 11 may be any of the label embodiments discussed herein. As shown, some of the antibody binding protein 12 is bound to anti-species antibody 15 at particular sites, while at other sites, some the antibody binding protein 12 are free for future binding to an analyte receptor or test line capture agent antibody 37 (not shown). The analyte receptor label complex anti-species antibody 15 has affinity to control line capture agent antibody 16. For instance, FIG. 6 shows two sites where the analyte receptor label complex anti-species antibody 15 has affinity to control line capture agent antibody 16. Other embodiments of the analyte-receptor label complex include more than one site of the various binding complexes discussed herein and illustrated in FIG. 6.

Figure 7:
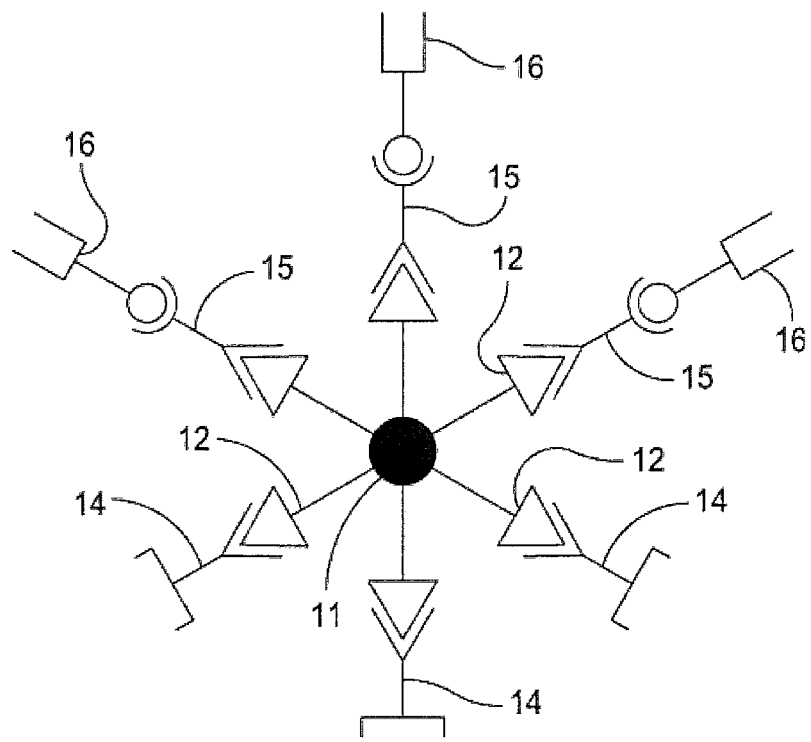
FIG. 7 is another isolated schematic view of a label complex and analyte receptor embodiment.

FIG. 7 shows one modified embodiment of an analyte-receptor label complex illustrated in FIG. 6, with the addition of an analyte receptor 14 at one site. For instance, at least one site of the analyte-receptor label complex may include an antibody binding protein 12 that is bound to an analyte receptor 14. Typically, the analyte receptor 14 has an affinity to an analyte and a test line capture agent. As further shown, at least one site of the analyte-receptor label complex may include an antibody binding protein 12 that is bound to anti-species antibody 15. And as illustrated, the anti-species antibody 15 has affinity to control line capture agent antibody 16. Additionally, at least one site of the analyte-receptor label complex may include an antibody binding protein 12 that is free for future binding to an analyte receptor (not shown). Other embodiments of the analyte-receptor label complex include more than one site of the various binding complexes discussed herein and illustrated in FIG. 7.

Figure 8:
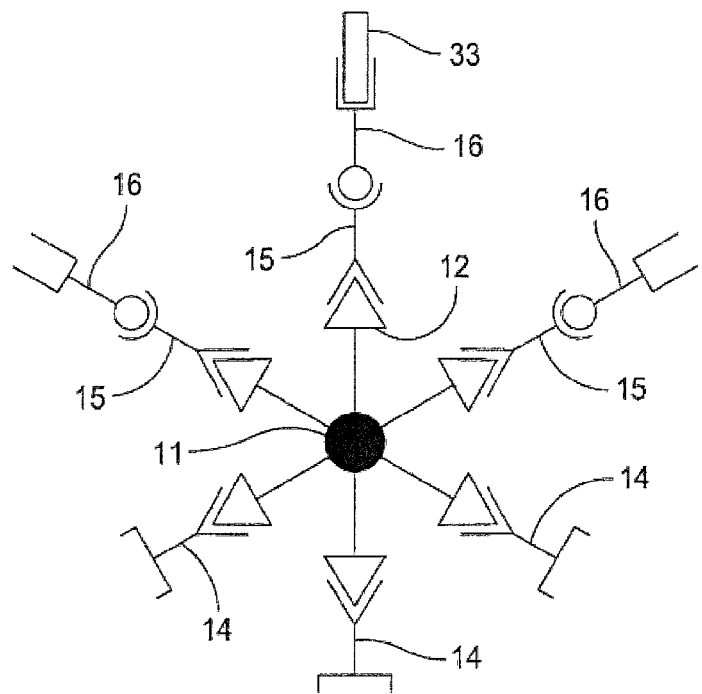
FIG. 8 is another isolated schematic view of a label complex embodiment with an analyte receptor and a control line capture agent.

FIG. 8 shows one modified embodiment of an analyte-receptor label complex illustrated in FIG. 7, with the addition of a control line capture agent antibody 16 being bound to a control line capture agent 33 on one site. As further shown, at least one site of the analyte-receptor label complex may include an antibody binding protein 12 that is bound to an analyte receptor 14. Typically, the analyte receptor 14 has an affinity to an analyte and a test line capture agent. As further shown in FIG. 8, at least one site of the analyte-receptor label complex may include an antibody binding protein 12 that is bound to anti-species antibody 15. And as illustrated, the anti-species antibody 15 may have an affinity to control line capture agent antibody 16. Additionally, at least one site of the analyte-receptor label complex includes an antibody binding protein 12 that is free for future binding to an analyte receptor (not shown). Other embodiments of the analyte-receptor label complex include more than one site of the various binding complexes discussed herein and illustrated in FIG. 8.

Figure 9:
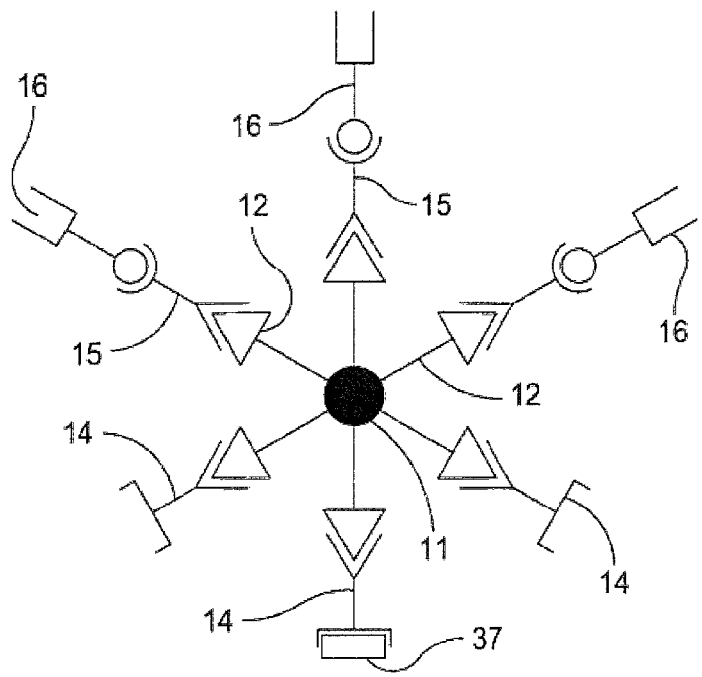
FIG. 9 is yet another isolated schematic view of a label complex embodiment with an analyte receptor, control line capture agent and an analyte/test line capture agent.

FIG. 9 shows one modified embodiment of an analyte-receptor label complex 35 illustrated in FIG. 8, with the addition of an analyte-receptor 14 being bound by analyte 37 on one site. As shown, on at least one site, the antibody 16 to control line capture agent 33 is unbound by a control line capture agent as shown in FIG. 8. Again, on this particular site, some of the antibody binding protein 12 is bound to anti-species antibody 15. The anti-species antibody 15 may have an affinity to control line capture agent antibody 16. In yet other sites, the analyte-receptor label complex may include an antibody binding protein 12 that is bound to an analyte receptor 14. Typically, the analyte receptor 14 has an affinity to an analyte and a test line capture agent. Other embodiments of the analyte-receptor label complex include more than one site of the various binding complexes discussed herein and illustrated in FIG. 9.

Figure 10:
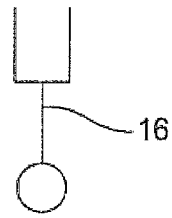
FIG. 10 is an isolated representative of a control line capture agent embodiment, for instance showing antibody to control line capture agent.
Figure 14:
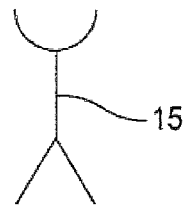
FIG. 14 is an isolated representative of an anti-species antibody embodiment.
Figure 11:
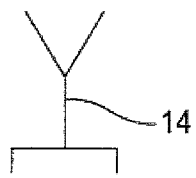
FIG. 11 is an isolated representative of an analyte receptor and test line capture agent antibody embodiment.
Figure 15:
FIG. 15 is an isolated representative of a label embodiment.
Figure 12:
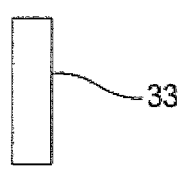
FIG. 12 is an isolated representative of a control line capture agent embodiment.
Figure 16:
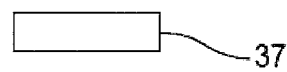
FIG. 16 is an isolated representative of a test line capture agent/analyte.
Figure 13:
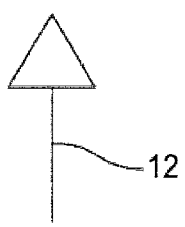
FIG. 13 is an isolated representative of antibody binding protein embodiment.

FIGS. 10-16 show various isolated components useful for lateral flow apparatus discussed herein. For instance, FIG. 10 is an isolated view of an antibody to control line capture agent 16, including any of the embodiments discussed herein. Further, FIG. 11 shows an analyte receptor 14, including any of the embodiments discussed herein. FIG. 12 illustrates a control line capture agent 33, including any of the embodiments discussed herein. FIG. 12 shows an antibody binding protein 12, including any of the embodiments discussed herein. FIG. 14 illustrates an anti-species antibody 15, including any of the embodiments discussed herein. Additionally, FIG. 13 shows label 11, including any of the embodiments discussed herein. Finally, FIG. 16 shows one example of a test area capture agent 37 of any of the embodiments discussed herein; however, as discussed above, FIG. 16 may also representative of an analyte.

Particular examples of the label complexes and apparatus described herein may be used to detect allergenic proteins. For instance, casein and β-lactoglobulin allergenic proteins may be detected from food sources, including milk sources, with the label complexes and apparatuses. However, the label complexes and apparatus described herein may be useful for detecting allergenic proteins in other food sources, including grains, nuts, eggs and the like.

In use, the presence or absence tests provided by the apparatuses introduced above, and similar threshold level tests, provide qualitative analysis, providing a "yes" or "no" result. Those skilled in the art will recognize that tests that detect the presence or absence of analyte above, or below, a certain threshold level are known as semi-quantitative tests or threshold level tests. Tests that determine that a target analyte is present at a particular concentration, or within a range of concentrations, are known as quantitative tests. Although quantitative tests may determine that an analyte is present within a range of concentrations or at a particular level the results also have a range of error. For example, a result that an analyte is present at 5 parts per million (ppm) can be within a range of acceptable error, for example a result of 5 ppm can mean that analyte is present in a range of 2-8 ppm. Such a test is referred to as quantitative. Tests that provide quantitative results within a limited range are also described as quantitative. For example, results may indicate that an analyte is present within a range of 0 to 20 ppm but above 20 ppm typically no conclusion can be drawn, other than that the result is above 20 ppm.

In certain exemplary methods, the sample may be contacted to sample application pad 1. For instance, sample may flow downstream from sample application pad 1 to POREX 7 containing mobile phase receptor. A portion of receptor will bind analyte from the sample and flow along the nitrocellulose membrane 3 to at least one test line 4. A portion of receptor unbound by sample analyte will bind to at least one of the test lines 4. The remaining unbound receptor and analyte-receptor complex will then flow downstream to at least one control line 5. A portion of said unbound receptor and a portion of analyte-receptor complex will then bind at the at least one control line 6. The remaining unbound receptor, or analyte-receptor complex, will flow downstream to the absorbent pad 6. The at least one control line 5 may be compared to the at least one test line 4 to determine at least one result.

In one particular method, an antibody for an analyte is mixed with a sample to create a sample mixture. The sample mixture is then incubated. During incubation, analyte from the sample is combined, and/or mixed, for example by vortexing, with antibody. The sample mixture is then applied to test strip 8, upon which the label complex 35 has previously been applied to create a mobile phase that includes the sample mixture and the label complex 35. In particular examples, the label complex 35 includes gold labeled protein A that is previously bound to an antispecies antibody, such as rabbit antimouse, which is in turn bound to a mouse antibody. For instance, the mouse antibody is chosen for its sensitivity to a control line capture agent 33. When the sample mixture is combined with the label complex 35, antibody to the analyte can bind with protein A. The anti-species antibody can also be bound to the protein A. As such, the mobile phase becomes a mixture of label complex 35 bound to analyte antibody. In addition, depending on whether or not analyte is present in the sample, the analyte antibody will, in turn, be bound by analyte from the sample.

Typically, the mobile phase then flows to a test line. The capture agent immobilized at the test line has affinity to the analyte antibody, which affinity is the same or similar to that of the analyte in the test sample. Such a capture agent can be, for example, a representative analyte or analogue thereof that binds with similar affinity to the analyte antibody as does the analyte so that a "competition" can occur. Due to that similar affinity, capture agent at the test line can bind the label complex more efficiently if the analyte antibody is not bound by analyte from the sample. When the sample contains analyte, an analyte-antibody complex will form that wholly or partially prevents capture of the label complex at the test line. As the amount of analyte in the sample increases, less label complex is captured at the test line until the detectable signal resulting from binding at the test line approaches, or is at, background signal levels.

In one quantitative test, the changes in the at least one control area/zone and test area/zone determine the test range detection level of analyte. For instance, the changes in the at least one test line 4, and when at least one control line 5 is present, the extent of the difference between the or test lines, determine the test range detection level of analyte. To more accurately, and/or numerically, assess the differences and the binding at the control zone and test zone, particularly in a quantitative assay, a reader, such as a spectrophotometer or other reflectance/absorbance reader can be used to detect and/or measure the signal provided by a label, such as a chromogen, for example colloidal gold.

There are a number of possible methods for reading a result on a strip. In a strip with only one test line and one control line the control line can be compared to the test line. In a strip containing multiple test lines possible reading methods include: finding the difference in signal intensities between the control line and each of the test lines and adding the results; finding the difference in signal intensities between one test line and the control line; finding the difference in signal intensities between only one test line and control line for one set of conditions and the other test line and the control line for another set of conditions.

Using the sum of the difference in reflectance between the control line and the two test lines can provide a greater separation between results from a range of concentrations as compared to using only the difference between the control line and a single test line. Using the sum of the differences between the control lines and each of the two test lines, can also help to reduce testing error. For example, if an aberrant result occurred at one or the other test lines that result can be moderated by being combined with a second set of results. This can be particularly useful when quantitation at a particular concentration, or within a range of concentrations, occurs.

For quantitation, reflectance results can be converted to a concentration value for an amount of analyte. One method for converting reflectance to concentration can employ fitting the data to a curve using a formula, such as:

$$\text{concentration} = e^{\left(\frac{Result-c}{a}\right)} - b,$$

where a, b and c are constants determined by fitting the data to a curve.

The result is the value determined by comparing reflectance in the control line to reflectance at each of the test lines. For example, intensity values at each of the test lines can be separately deducted from intensity value at the control line and the two differences added together to arrive at the result. A look-up table can also be used to convert the mathematical result to a concentration value for the analyte.

In another embodiment, the test can be used not only as a quantitative test in which a reader provides a result in, for example, parts per million (ppm) levels but also a qualitative result. For example, the control line can be compared visually with the first test line to determine that an analyte is present above a certain threshold level, for example above 2 ppm or above 5 ppm.

For lateral flow assays, the sample or, if extraction is required, the sample extract, can be mixed with a dilution buffer prior to combining with the analyte-receptor. The dilution buffer may be needed to allow a mobile phase to flow uniformly over the test strip and/or allows reconstitution of the previously applied, for example, dried reagents, on the test strip. The extract can be diluted by a number of methods and a variety of possible dilution ratios of the extract with the dilution buffer. The dilution buffer can consist of, for example, BSA solution, buffer or water. When the analyte is in sample liquid, such as fluid milk, the sample may not require dilution or extraction. Dilutions or extractions, however, may still be desirable such as to alter the test sensitivity range or to allow consistency between samples.

In one example, to detect the presence or absence of an analyte, or an analyte at a threshold level, the test strips 8 generally provide a signal that can be observed visually, such as through color changes or color differences on the test strip. In yet other methods, the signal is observed, measured and/or interpreted visually or with a reader. A variety of readers are appropriate, depending on the detectable component used, including spectrophotometers, LCD cameras, reflectance readers, luminometers, fluorometers, scintillation counter, magnetic detectors and other instruments capable of reading, measuring and/or interpreting changes on a lateral flow test strip. One such instrument is described in U.S. Pat. No. 6,124, 585, issued Sep. 26, 2000, hereby incorporated by reference in its entirety. Another such instrument is a ROSA Reader (ROSA is a registered trademark of Charm Sciences, Inc., Lawrence, Mass.).

In particular methods, the sample alone, or along with reagent(s), can be incubated prior to addition to the test strip 8. Alternatively, the sample and reagent can be incubated after application to the test strip 8, such as during the running of at least one test. The sample and reagent, alone or together, can also be incubated both before application to the test strip 8. Yet in other examples, the sample and reagent may be incubated after application to the test strip 8. For instance, the sample and reagent may be incubated during the running of the test, while the mobile phase is flowing on the test strip 8. In yet other embodiments, at least a one or more of the mobile phase reagents can be premixed with the sample and some reconstituted from the test strip 8 by the addition of the sample and some of the reagents. By premixing at least one or more of the reagents with the sample, incubation of such mixture can take place prior to addition to the test strip. That allows not only a pre-incubation but also, if desirable, a pre-reaction of certain reagents with the sample. In additional examples, multiple reagents are premixed with the sample. Further, in the case of detection of large analytes, such as allergenic proteins, or other molecules that require extended time to bind to related receptor, unexpected success has been discovered with incubation of the sample suspected of containing the analyte with the specific receptor for that analyte prior to addition to the test strip.

In additional exemplary methods, a pipette having a premeasured volume is pipetted onto the lateral flow apparatus, for instance onto the sample application pad 1 of the strip 8. However, in yet another embodiment, rather than pipette a pre-measured volume onto the lateral flow apparatus, the apparatus is arranged to be dipped into a sample to absorb a selected amount of the sample. In one example, a sample is absorbed onto a swab-like device and mixed with reagents for pre-incubation, such as in a vial, after which time all or a portion of the contents of the vial are contacted with lateral flow apparatus. An example of such a swab like device is known as POCKETSWAB or POCKETSWAB Plus, available from Charm Sciences, Inc., and described in U.S. Pat. No. 5,965,453, issued Oct. 12, 1999, and incorporated herein by reference in its entirety, (although typical POCKETSWAB devices detect, for example, adenosine triphosphate for hygiene monitoring, the non-biochemical components can be used for sampling, mixing and incubating applications such as described herein).

Although, many of the herein examples and descriptions refer to detecting allergenic proteins, such as casein and beta-lactoglobulin, other analytes can be detected in a variety of matrices using the herein described methods and devices.

The following experiments demonstrate the efficacy and utility of the present inventions.

Example 1

POCKETSWAB Format

A POCKETSWAB (POCKETSWAB is a registered trademark of Charm Sciences, Inc. Lawrence, Mass.) test device can be used for sampling and incubation. The PocketSwab niblet can include dilution buffer and the vial include a tablet or freeze dried powder containing the analyte receptor, for example the antibody to the allergen.

After incubating and mixing within the POCKETSWAB the sample-receptor mixture can be added to a lateral flow test strip. The label complex can include gold beads sprayed onto POREX with protein A bound to the gold beads along with a rabbit anti-mouse antibody in a concentration or a configuration that will allow only a portion of the protein A binding sites to be bound by the rabbit anti-mouse antibody. Also included was a mouse antibody that would bind to the rabbit anti-mouse antibody. The lateral flow test strip has a BSA-analyte conjugate designed to capture the analyte-receptor if not bound by analyte from the sample.

The swab is removed from the POCKETSWAB and paced in a liquid sample and then replaced back into the POCKETSWAB and twisted down through the foil barriers to allow the dilution buffer to dissolve the pellet on the bottom of the tube. The POCKETSWAB is then shaken and incubated for 5 minutes at 45° C. After the 5 minutes, the vial is unscrewed from the bottom of the POCKETSWAB and a polypipet used to pipet 300 µl of the incubated sample mixture onto the lateral flow test strip. The lateral flow test strip is then incubated for 5 minutes and then inspected visually and read in a reader.

During the first incubation step the analyte if present becomes bound to the analyte receptor, in this case antibody to the analyte. The antibody to the analyte is then present either as free antibody or antibody-analyte combination, both having affinity to the protein A—gold bead portion of the label complex. The gold-protein A—free antibody is able to bind to its binding partner at the test line. The label complex-antibody-analyte combination cannot bind to the test line. The label complex which passes the test line can then bind to the control line which includes a binding partner for the monoclonal antibody portion of the label complex which is bound to the label complex through a rabbit-anti-mouse antibody. Although not wishing to be constrained by theory, it is theorized that the label complex provides an additional spacer arm for more effective binding to the control line by avoiding steric interference from the large analyte molecule such as casein and/or beta-lactoglobulin.

For a positive sample the number of label complex bound to the test line is less than the number of label complex bound to the control line. For a negative sample the test line has more label complex bound than the control line. The reader is able to convert the number of label complex at each line or its line intensities to determine if the sample is positive or negative at a defined threshold point or provide a numerical value over a defined test range.

Example 2

To form gold beads, 1 milliliter (mL) of a filtered 40 milligram (mg)/ml gold chloride solution is added to 360 ml of boiling water in a clean one liter flask. To 35 ml of water was added 3.5 ml of 1% sodium citrate solution. The citrate solution was added to the gold solution while boiling. After refluxing for 20 to 30 minutes the bead solution was cooled and brought to pH 8.2 with potassium carbonate.

Protein A (500 µl of 1 milligram per milliliter (mg/ml) solution in 2 millimolar (mM) diethanolamine buffer, pH 8.0 was added to 375 ml of pH 8.2 gold beads. After 10 minutes the protein A beads were blocked with in-house BSA blocking buffer for at least one hour. Rabbit anti-mouse antibody (100 µl of a 1 mg/ml solution from Bethyl Laboratories) was then added to the gold beads and incubated for 20 minutes followed by 175 microliters (µl) of cloxacillin purified monoclonal antibody. After another 20 minutes incubation the beads were centrifuged for 50 minutes at 8500 rpm. The beads were then dissolved in water and 0.5 ml of the BSA blocking buffer and diluted further to give a ultraviolet 530-535 nanometer (nm) of 0.167 when adding 10 µl of beads in 3 ml water. Glycerol (2 ml) was then added. The beads were then further diluted in a bead spray solution consisting of 40% sucrose, 10% BSA in 20 mm sodium phosphate at pH 7.2 with Proclin 300 added as a preservative. The beads were sprayed onto POREX treated with 2 mM borate, 0.1M NaCl, 1% sucrose, 0.0025% SDS and 0.05 mg/ml glutathione at pH 7.4 and dried.

The gold-protein A was sprayed (4 lines at 0.8 µl/cm) using a BIODOT sprayer onto POREX. The POREX was pretreated with 2 mM borate at pH 7.4, containing 0.1 M NaCl, 1% sucrose, 0.0025% SDS and 0.05 mg/ml reduced glutathione and dried.

The test line with test lines and the control line with a control line were sprayed onto a SARTORIUS UNISART CN-140 nitrocellulose membrane (Sartorius and Unisart are registered trademarks of Sartorius AG, Gottingen, Germany). The test and control lines were sprayed onto the nitrocellulose with a BIODOT sprayer.

To prepare control line reagent cloxacillin-Bsa was prepared as described in U.S. Pat. No. 7,863,057 incorporated herein by reference in its entirety.

For the test line, bovine serum albumin was first purified using a Sephacryl S-200 column (2.5 by 113 cm). The monomer fraction was retained and reacted with sulfo-SMCC (sulfosuccininimidyl 4-(N-maleimdiomethyl)-cyclohexane-1-carboylate purchased from ThermoScientific) for 2 hours at pH 7.6 and then desalted in a HiPrep 26/10 desalting column from GElifesciences by FPLC. Either beta-lactoglobulin or casein (depending on the which is to be detected) were reacted with Traut's reagent (Traut's purchased from Thermo Scientific and beta-lactoglobulin and casein purchased from Sigma) for 30 minutes at room temperature (RT). The pH was adjusted to pH 6.8 and in a separate reaction the S-SMCC activated BSA casein was reacted overnight. The reactions were concentrated and again subjected to Sepharcyl S-200 chromatography in separate runs. Fractions were collected and sprayed onto NC to determine which showed binding to labeled antibody and thus the ability to compete for test line binding with the corresponding analyte.

Casein Test Line

Test line was sprayed onto the NC with 27× dilution casein-BSA in 20% sucrose. The control line was sprayed with 100×BSA cloxacillin in 20% sucrose Beta-Lactoglobulin Test Line Test line was sprayed with 30× dilution beta-lactoglobulin-Bsa in 20% sucrose. The control line was sprayed with 80× dilution BSA-cloxacillin in 20% sucrose.

Antibody Purification

Each rabbit antibody was purified by affinity chromatography column as is well known in the art.

Assay Format

The stock solution consisted of 10 µl of purified antibody added to 1 ml of dilution buffer (2% BSA, 0.03% pluronic, 0.217% proclin 300 in 20 mM sodium phosphate at pH 6.8).
Beta-lactoglobulin assay: 30 µl of stock beta-lactoglobulin antibody was added to 0.5 ml of dilution buffer.
Casein assay: 25 µl of the stock casein antibody was added to 0.5 ml dilution buffer.

A powdered milk tablet was mixed with 10 ml water to yield a 5 parts per million (ppm) concentration and then diluted to 1 ppm or 2.5 ppm with water. A 150 µl portion of sample was added to each assay tube and incubated for 5 minutes at 45° C. A 300 µl portion was then added to the lateral flow test strip and incubated for 5 minutes at 45° C. (using the Charm lateral flow incubator). After incubation the test strips were read in a Charm Pearl Reader which measures the intensity of the lines and provides a negative or positive result including a numerical result.

The lateral flow strips were also visually evaluated. T line is the test line and C line is the control line. Results were obtained for zero, 1, 2.5 and 5 ppm.

Beta-lactoglobulin assay

| ppm PM | T line | C line | Reader | Reader | Visual |
|---|---|---|---|---|---|
| 0 | 3458 | 2018 | −1540 | Neg | Neg |
| 0 | 3627 | 2378 | −1349 | Neg | Neg |
| 0 | 3339 | 1897 | −1542 | Neg | Neg |
| Ave | 3475 | 2098 | −1477 | | |
| 1 | 2705 | 2342 | −463 | Neg | Neg |
| 1 | 2795 | 2212 | −683 | Neg | Neg |
| 1 | 2988 | 2274 | −814 | Neg | Neg |
| Ave | 2829 | 2276 | −653 | | |
| 2.5 | 2084 | 2625 | 841 | Pos | Pos |
| 2.5 | 1936 | 2994 | 1358 | Pos | Pos |
| 2.5 | 1914 | 2643 | 1029 | Pos | Pos |
| Ave | 1978 | 2754 | 1076 | | |
| 5 | 1099 | 2860 | 2061 | Pos | Pos |
| 5 | 1467 | 2843 | 1676 | Pos | Pos |
| 5 | 1266 | 2716 | 1750 | Pos | Pos |
| | 1277 | 2806 | 1829 | | |

Casein Assay

| ppm PM | T line | C line | Reader | Reader | Visual |
|---|---|---|---|---|---|
| 0 | 3557 | 2188 | −1369 | Neg | Neg |
| 0 | 4006 | 2253 | −1753 | Neg | Neg |
| 0 | 3535 | 2104 | −1431 | Neg | Neg |
| Ave | 3699 | 2182 | −1518 | | |
| 1 | 2453 | 1824 | −629 | Neg | Neg |
| 1 | 2294 | 1761 | −533 | Neg | Neg |
| 1 | 2361 | 1753 | −608 | Neg | Neg |
| Ave | 2369 | 1779 | −590 | | |
| 2.5 | 1901 | 1836 | −65 | Nes | Neg |
| 2.5 | 1672 | 2294 | 622 | Pos | Pos |
| 2.5 | 1642 | 2365 | 723 | Pos | Pos |
| Ave | 1738 | 2165 | 427 | | |
| 5 | 1228 | 1955 | 727 | Pos | Pos |
| 5 | 1005 | 1947 | 942 | Pos | Pos |
| 5 | 1161 | 2559 | 1398 | Pos | Pos |
| | 1131 | 2154 | 1022 | | |

Unexpectedly, the results reflect that both assays can detect either casein or beta-lactoglobulin at 2.5 ppm and 5.0 ppm. Although the inhibition of the test line was slightly better for casein, possibly due to the greater level of casein concentration in milk, the beta-lactoglobulin assay provided an overall difference between test line and control line due largely to improved control line binding.

Example 3

Allergen assay to detect casein in powdered milk in three line (two test line) format. Test line #1: 37.7× diluted BSA-casein; test line #2: 8× diluted BSA-casein; control line: 44× diluted BSA-cloxacillin Differences from above: Difference from example 2 was that for this assay 160 µl of sample was added directly to the vial and 30 µl of the stock antibody was used to added to the dilution buffer.

| Conc | | T1 | T2 | C | Result |
|---|---|---|---|---|---|
| 0 | | 4650 | 2616 | 1270 | −4726 |
| | | 4044 | 2601 | 1613 | −3419 |
| | | 3821 | 2614 | 1900 | −2635 |
| | | 3875 | 2582 | 1714 | −3029 |
| | AVE | 4098 | 2603 | 1624 | −3452 |

-continued

| Conc | | T1 | T2 | C | Result |
|---|---|---|---|---|---|
| 0.5 | | 3441 | 2323 | 1511 | −2742 |
| | | 3614 | 2715 | 2155 | −2019 |
| | | 2722 | 2442 | 1686 | −1792 |
| | | 3684 | 2298 | 1428 | −3126 |
| | AVE | 3365 | 2445 | 1695 | −2420 |
| 1 | | 3396 | 2695 | 2201 | −1689 |
| | | 2429 | 2314 | 1938 | −867 |
| | | 2707 | 2138 | 1904 | −1037 |
| | | 2738 | 2513 | 2121 | −1009 |
| | AVE | 2818 | 2415 | 2041 | −1151 |
| 2.5 | | 2073 | 1782 | 1635 | −585 |
| | | 2288 | 2061 | 2220 | 91 |
| | | 2224 | 2183 | 2187 | −33 |
| | | 2138 | 2125 | 2098 | −67 |
| | AVE | 2181 | 2038 | 2035 | −149 |
| 5 | | 2009 | 1967 | 2282 | 588 |
| | | 1929 | 1583 | 1988 | 464 |
| | | 1419 | 1598 | 1771 | 525 |
| | | 1711 | 1609 | 2207 | 1094 |
| | AVE | 1767 | 1689 | 2062 | 668 |
| 10 | | 774 | 1288 | 1918 | 1774 |
| | | 1102 | 1273 | 1828 | 1281 |
| | | 945 | 1012 | 2093 | 2229 |
| | | 1203 | 1382 | 2328 | 2071 |
| | AVE | 1006 | 1239 | 2042 | 1839 |

Note:
larger difference between control line and test line for the casein assay with the 3 line test. The reader can be calibrated to give a quantitative value based on the overall reader result.

Example 4

| powdered milk ppm | T line | C line | Reader | reader | visual |
|---|---|---|---|---|---|
| 0 | 3456 | 1653 | −1803 | neg | neg |
| 0 | 3644 | 1844 | −1800 | neg | neg |
| 0 | 3535 | 1510 | −2025 | neg | neg |
| AVE | 3545 | 1669 | −1877 | | |
| 5 | 1913 | 2650 | 737 | pos | pos |
| 5 | 1754 | 2810 | 1056 | pos | pos |
| 5 | 1815 | 2900 | 1085 | pos | pos |
| AVE | 1827 | 2887 | 959 | | |

The above Example 4 results were obtained using Pocketswab format with the NC at 20×BSA-beta-lactoglobulin and 30× cloxacillin-BSA.

In this case the antibody was in tablet form within POCKETSWAB device vial. Swab was dipped in to sample solution either water (0 ppm) or 5 ppm powdered milk for 20 seconds and then reinserted into the swab. Swab was screwed down to puncture the first foil seal containing 500 μl of dilution buffer and then the second seal allowing contact of the sample with a tablet containing the beta-lactoglobulin antibody. The sample was then vortexed for 20 seconds to generate a complete mixing of the tablet and sample. The sample was then incubated for 10 minutes at 45° C. The vial was unscrewed from the pocketswab and 300 μl was then withdrawn with a polypipet and added to the lateral flow strip. The lateral flow strip was then incubated at 45° C. for 5 minutes. The strip was then read in the reader and visually evaluated.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. For instance, herein examples and descriptions refer to detecting allergenic proteins, such as casein and beta-lactoglobulin, but other analytes can be detected in a variety of matrices using the herein described label complexes, apparatus and methods. It is further noted that, as used in this application, the singular forms "a," "an," and "the" include plural referents unless expressly and unequivocally limited to one referent.

What is claimed is:

1. A lateral flow test strip for the analysis of one or more analytes in a liquid sample, the test strip comprising:
   a) a label complex, the label complex including:
      (i) at least two antibodies, one of the at least two antibodies including an antispecies antibody and another of the at least two antibodies including an antibody having a sensitivity to the antispecies antibody and to a control line capture agent, the control line capture agent being bound to a control line and characterized in that the control line capture agent has affinity to the label complex independent of the label complex being bound by the one or more analytes;
      (ii) at least one bound antibody binding protein having affinity to the anti-species antibody;
      (iii) at least one free antibody binding protein adapted to bind to at least one receptor for the one or more analytes; and
      (iv) a detectable component being bound to the at least one bound antibody binding protein and to the at least one free antibody binding protein; and
   b) a solid support, the solid support supporting the label complex, the control line and at least one test line having a test line capture agent immobilized thereon, wherein the solid support comprises a body adapted to traverse lateral flow and a surface to provide a detectable signal, whereby the detectable signal generates an intensity when the at least one analyte receptor is captured by either the control line capture agent or the test line capture agent.

2. The test strip of claim 1, wherein the at least one analyte receptor has affinity to the one or more analytes and to the test line capture agent.

3. The test strip of claim 2, wherein any of the at least one analyte receptors not bound to the one or more analytes will bind to the test line capture agent.

4. The test strip of claim 1, wherein a greater intensity of the detectable signal in the test line as compared to the control line indicates a negative result, and a greater intensity of the detectable signal in the control line compared to the test line indicates a positive result.

5. The test strip of claim 1, wherein the test line capture agent has greater binding affinity to the label complex when the label complex is unbound by the one or more analytes.

6. The test strip of claim 1, wherein each of the at least one analyte receptors comprises an antibody with sensitivity to one of the one or more analytes.

7. The test strip of claim 1, wherein the test line capture agent comprises a representative analyte or analog thereof.

8. The test strip of claim 1, wherein the one or more analytes comprises casein and wherein the at least one analyte receptor comprises an antibody to casein.

9. The test strip of claim 1, wherein the one or more analytes comprises beta-lactoglobulin and wherein the at least one analyte receptor comprises an antibody to beta-lactoglobulin.

10. The test strip of claim 1, wherein the one or more analytes comprise casein and beta-lactoglobulin and the test strip comprises two analyte receptors and two test lines, wherein at least one of the analyte receptors comprises antibody to casein and at least one of the other analyte receptor comprises antibody to beta-lactoglobulin.

11. The test strip of claim 1, wherein the one or more analytes comprise casein and beta-lactoglobulin and the test strip comprises two analyte receptors and two test lines, wherein at least one of the analyte receptors comprises antibody to casein and the other analyte receptor comprises antibody to beta-lactoglobulin, wherein one test line comprises a capture agent with sensitivity to the antibody to casein and the other test line comprises capture agent with sensitivity to the antibody for beta-lactoglobulin.

\* \* \* \* \*